United States Patent [19]
Renshaw et al.

[11] Patent Number: 5,958,896
[45] Date of Patent: Sep. 28, 1999

[54] CYTIDINE-CONTAINING AND CYTOSINE-CONTAINING COMPOUNDS AS TREATMENTS FOR STIMULANT EXPOSURE

[75] Inventors: Perry F. Renshaw, Arlington; Scott Lukas, Belmont, both of Mass.

[73] Assignee: The McLean Hospital, Belmont, Mass.

[21] Appl. No.: 08/908,997

[22] Filed: Aug. 8, 1997

[51] Int. Cl.$^6$ ......................... A61K 31/70; A61K 31/505
[52] U.S. Cl. ........................... 514/49; 514/274; 514/812
[58] Field of Search ............................ 514/49, 812, 274

[56] References Cited

PUBLICATIONS

Teoh, S.K. et al., *J. Clin. Psychopharmacology*, 1993; 13: 87–99, Acute Interactions of Buprenorphine with Intravenous Cocaine and Morphine: An Investigational New Drug Phase I Safety Evaluation.

Maas, L.C. et al., *Am J Psychiatry*, 1998; 155(1):124–126, Functional Magnetic Resonance Imaging of Human Brain Activation During Cue–Induced Cocaine Craving.

English, C.D., et al., *Biol Psychiatry*, 1997; 41:500–502, Elevated Frontal Lobe Cytosolic Chloine Levels in Minimal or Mild AIDS Dementia Complex Patients: A Proton Magnetic Resonance Spectroscopy Study.

Sholar, M.B., et al., *Journal of Clinical Endocrinology and Metabolism*, 1998; 83(3):966–968, Concurrent Pharmacokinetic Analysis of Plasma Cocaine and Adrenocorticotropic Hormone in Men.

Kaufman, M. J., et al., *JAMA*, 1998; 279(5):376–380, Cocaine–Induced Cerebral Vasoconstriction Detected in Humans with Magnetic Resonance Angiography.

Brown et al., "CNS Complications of Cocaine Abuse: Prevalence, Pathophysiology, and Neuroradiology," *AJR Am. J. Roentgenol.*, 159:137–147 (1992).

Chang et al., "Neurochemical Alternations in Asymptomatic Abstinent Cocaine Users: A Proton Magnetic Resonance Spectroscopy Study," *Biol. Psychiatry*, 42:1105–1114 (1997).

Hoff et al., "Effects of Crack Cocaine on Neurocognitive Function," *Psychiatry Res.*, 60:167–176 (1996).

Jacobs et al., "Cocaine Abuse: Neurovascular Complications," *Radiology*, 170:223–227 (1989).

Kreek, "Opiate and Cocaine Addictions: Challenge for Pharmacotherapies," *Pharmacol. Biochem. Behav.*, 57:551–569 (1997).

McCance, "Overview of Potential Treatment Medications for Cocaine Dependence," *NIDA Res. Monogr.*, 175:36–72 (1997).

Peterson et al., "Neurovascular Complications of Cocaine Abuse," *J. Neuropsychiatry Clin. Neurosci.*, 3:143–149 (1991).

Warner et al., "Pharmacotherapy for Opioid and Cocaine Abuse," *Med. Clin. North Am.*, 81:909–925 (1997).

Saligaut, C. et al., *Neuropharmacology*, 1987; 26(9):1315–1319, Circling Behaviour in Rats with Unilateral Lesions of the Nigrostriatum Induced by 6–Hydroxydopamine: Changes Induced by Oral Administration of Cytidine–5'–Diphosphocholine.

O'Rourke, M.M. et al., *Life Sciences*, 1996; 59(2), 119–130, Effect of Chronic Cocaine Exposure on Carotid Artery Reactivity in Neonatal Rabbits.

Christensen, J.D. et al., *Magnetic Resonance in Medicine*, 1996; vol. 35:658–663, Abnormal Cerebral Metabolism in Polydrug Abusers During Early Withdrawal: A $^{31}$P MR Spectroscopy Study.

London, E.D. et al., *Res. Comm. Subst. Abuse*, 1989; 10:141–144, Cerebral Glucose Utilization in Human Heroin Addicts: Case Reports from a Positron Emission Tomographic Study.

Levin, J.M. et al., *J. Nucl. Med.*, 1995; 36:1211–1215, Improved Regional Cerebral Blood Flow in Chronic Cocaine Users Treated with Buprenorphine.

Agnoli, A. et al., Novel Biochemical, Pharmacological and Clinical Aspects of Cytidinediphosphocholine, New York, NY: Elsevier Science Publishing Co., Inc., 1985; 30:305–315, Efficacy of CDPcholine in Chronic Cerebral Vascular Diseases (CCVD).

Boudouresques, B.A. et al., International Symposium: Brain Suffering and Precursors of Phospholipids: Paris, Jan. 18, 1980, Therapeutic Conduct in Light of a Cerebral Vascular Accident and the Use of CDP–Choline.

Centrone, G. et al., *Minerva Med.*, 1986; 77:371–373, Use of Citicoline in High Dosages in Acute Cerebrovascular Disease.

Moglia, A. et al., *Curr Ther Res.*, 1984; 36:309–313, Citicoline in Patients with Chronic Cerebrovascular Diseases (CCVD): Quantitative EEG Study.

Salvadorini, F. et al., *Curr Ther Res.*, 1975; 18:513–520, Clinical Evaluation of CDP–Choline (Nicholin®): Efficacy as Antidepressant Treatment.

Tazaki, Y. et al., *Stroke*, 1988; 19:211–216, Treatment of Acute Cerebral Infarction with a Choline Precursor in a Multicenter Double–Blind Placebo–Controlled Study.

Babb, S.M. et al., *Psychopharmacology* 1996; 127:88–94, Differential Effect of CDP–Choline on Brain Cytosolic Choline Levels in Younger and Older Subjects as Measured by Proton Magnetic Resonance Spectroscopy.

Gallai, V. et al., *Psychopharmacology* 1991; 103:1–5, Study of the P300 and Cerebral Maps in Subjects with Multi–Infarct Dementia Treated with Cytidine.

Galletti, P. et al., *J Neurol. Sci.*, 1991; 103:S19–S25, Biochemical Rationale for the Use of CDP–Choline in Traumatic Brain Injury: Pharmacokinetics of the Orally Administered Drug.

(List continued on next page.)

*Primary Examiner*—Phyllis G. Spivack
*Attorney, Agent, or Firm*—Clark & Elbing LLP

[57] ABSTRACT

Disclosed herein is a method for reducing stimulant dependencies in mammals that involves administration of a therapeutically-effective amount of a cytosine-containing or cytidine-containing compound, such as CDP-choline.

27 Claims, 10 Drawing Sheets

OTHER PUBLICATIONS

Weiss, G.B., *Life Sci.,* 1995; 56:637–660: Metabolism and Actions of CDP–Choline as an Endogenous Compound and Administered Exogenously as Citicoline.

Cohen, Bruce M. et al., *JAMA,* 1995; vol. 274, No. 11, 902–907, Decreased Brain Choline Uptake in Older Adults, An In Vivo Proton Magnetic Resonance Spectroscopy Study.

Secades, J.J. et al., *Methods Find. Exp. Clin. Pharmacol.* 1995 ; 17 (Suppl B):1–54, CDP–Choline: Pharmacological and Clinical Review.

Self, David W. et al., *Science,* 1996; 271:1586–1589, Opposite Modulation of Cocaine–Seeking Behavior by $D_1$–and $D_2$–Like Dopamine Receptor Agonists.

Citicoline Sodium (CDP–Choline), Investigator's Brochure, Revised: Apr. 1994 by Interneuron Pharmaceuticals, Inc.-

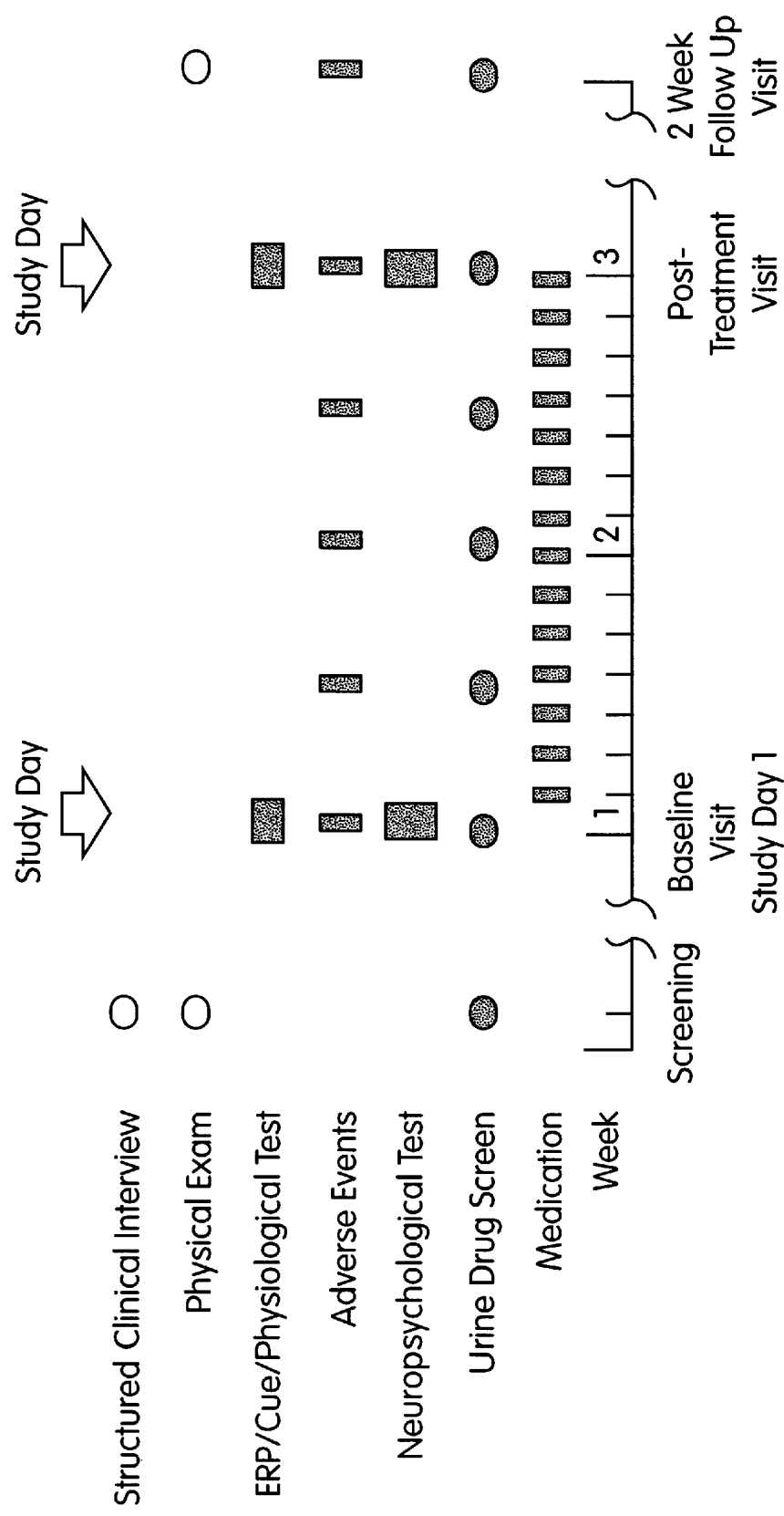

Effects of Cocaine or Placebo Administration on Cardiovascular Parameters

| Variable | Placebo (n=7) | | | 0.2 mg/kg Cocaine (n=9) | | | 0.4 mg/kg Cocaine (n=8) | | | ANOVA $F_{2,21}$ | $P$ |
|---|---|---|---|---|---|---|---|---|---|---|---|
| | Baseline | Peak | +20 min | Baseline | Peak | +20 min | Baseline | Peak | +20 min | | |
| HR | 63 ± 3 | 69 ± 3[b] | 64 ± 2* | 67 ± 2 | 105 ± 4[bb] | 85 ± 2[cc**] | 66 ± 3 | 112 ± 6[bb] | 98 ± 5[cc] | 15.0 | <0.002 |
| Sys | 129 ± 8 | 142 ± 7[b] | 133 ± 8** | 131 ± 5 | 152 ± 6[bb] | 137 ± 5** | 117 ± 4[a] | 147 ± 7[bb] | 98 ± 5[cc**] | 0.3 | 0.58 |
| Dias | 62 ± 3 | 71 ± 2[bb] | 66 ± 4 | 68 ± 3 | 89 ± 4[bb] | 78 ± 4[c**] | 74 ± 3[aa] | 94 ± 6[bb] | 87 ± 4[cc] | 5.1 | <0.05 |

Shown are means ± standard errors. ANOVA, repeated measures analysis of variance, testing for dose effect 20 min after drug administration versus baseline values. HR, heart rate, beats per minute; Sys and Dias, Systolic and Diastolic blood pressures, mm Hg.

[a] Significantly different from baseline for 0.2 mg/kg dose group, (p < 0.03, unpaired t-test)
[aa] Significantly different from baseline for placebo dose group, (p < 0.02, unpaired t-test)
[b] Significantly different from baseline within dose group, paired t-test p < 0.01
[bb] Significantly different from baseline within dose group, paired t-test p < 0.001
[c] Significantly different from baseline within dose group, paired t-test p < 0.02
[cc] Significantly different from baseline within dose group, paired t-test p < 0.002
* Significantly different from peak within dose group, paired t-test p < 0.05
** Significantly different from peak within dose group, paired t-test p < 0.005

Fig. 7

Magnetic Resonance Angiography Results

| Cocaine Dosage (mg/kg) | Angiography Rating | | | |
|---|---|---|---|---|
| | Unchanged | Ambiguous | Altered | Discordant Rating |
| 0.0 | 4 | 0 | 1 | 2 |
| 0.2 | 3 | 1 | 3 | 2 |
| 0.4 | 2 | 1 | 5 | 0 |

Shown are numbers of cases for each MRA rating category and cocaine dosage level.

Fig. 8

| Group: Measure: | Comparison (n=16) | HMI Methadone Maintenance (n=15) | HMI Short Term Maintenance (n=7) | HMI Long Term Maintenance (n=8) | HMI vs. Comparison unpaired t (df=29) | Short vs. Comparison unpaired t (df=21) | Long vs. Comparison unpaired t (df=22) | Short vs. Long unpaired t (df=13) |
|---|---|---|---|---|---|---|---|---|
| %PME | 8.9±0.9 | 10.1±1.4 | 10.8±1.5 | 9.5±1.1 | $p<0.008$ | $p<0.002$ | | |
| %Pi | 5.9±0.8 | 5.7±0.9 | 5.7±0.8 | 5.7±1.0 | | | | |
| %PDE | 30.2±2.3 | 33.2±3.9 | 35.5±4.0 | 31.2±2.5 | $p<0.02$ | $p<0.001$ | | $p<0.03$ |
| %PCr | 13.3±0.9 | 11.5±1.3 | 10.6±1.0 | 12.3±1.0 | $p=0.0001$ | $p<0.0001$ | $p<0.03$ | $p<0.01$ |
| %β-NTP | 10.7±1.3 | 10.1±1.3 | 10.1±1.3 | 10.1±1.3 | | | | |
| %Total NTP | 41.8±3.5 | 39.5±4.3 | 37.4±4.4 | 41.3±3.5 | | $p<0.02$ | | |
| PCr/Pi | 2.3±0.4 | 2.1±0.6 | 1.9±0.2 | 2.3±0.4 | | $p<0.02$ | | |
| β-NTP/PCr | 0.81±0.12 | 0.89±0.16 | 0.96±0.14 | 0.83±0.16 | | $p<0.02$ | | |
| PME/PDE | 0.30±0.02 | 0.30±0.03 | 0.30±0.02 | 0.30±0.03 | | | | |
| pH | 7.05±0.02 | 7.05±0.03 | 7.06±0.03 | 7.04±0.03 | | | | |

Fig. 9

CYTIDINE-CONTAINING AND CYTOSINE-CONTAINING COMPOUNDS AS TREATMENTS FOR STIMULANT EXPOSURE

BACKGROUND OF THE INVENTION

This invention relates to methods for the treatment of stimulant abuse and addiction.

In the mid-1980's, the use of the stimulant cocaine reached epidemic levels in the United States, and even today abuse of this drug remains widespread. In 1995, the Substance Abuse and Mental Health Administration reported that nearly 2.5 million Americans admitted occasional and 600,000 admitted frequent cocaine use. The adverse societal and health consequences stemming from such cocaine use are significant. First, there is the hidden toll of emotionally and psychologically damaged families dealing with a family member having a cocaine dependency. And second, there is the adverse exposure to potentially detrimental health consequences associated with cocaine use and abuse.

Although historically the frequency of hospital admissions associated with cocaine abuse has been relatively low (0.35–3%), hospital visits stemming from a cocaine-related event now appear to be on the increase. In addition, the case report literature illustrating catastrophic neurologic and cerebrovascular complications in cocaine users is also rapidly growing, and the incidence of cocaine-related strokes has been characterized as reaching epidemic proportions. Surprisingly, many cocaine-related deaths are not associated with any major brain pathology upon autopsy, yet patients have been observed to show signs associated with moderate to severe cognitive dysfunction.

Moreover, experts in this area have observed that even during periods of cocaine abstinence cognitive abnormalities persist, suggesting that brain dysfunction occurs and is maintained beyond the period of acute cocaine intoxication. The "clinically silent" nature of these abnormalities implies that substantial numbers of cocaine users may be afflicted with defects as yet undiagnosed. The etiologies of these subtle changes have not been elucidated, although cocaine-induced vasoconstriction and vasospasm have been implicated.

To date, there are no approved pharmacotherapies for cocaine abuse and dependence although the need for such therapies is clear.

SUMMARY OF THE INVENTION

In general, the invention features a method of treating a mammal exposed to a stimulant involving administering to the mammal, a therapeutically-effective amount of either a cytidine-containing or cytosine-containing compound.

In preferred embodiments, the mammal is a human; the stimulant is cocaine; the therapeutically effective compound is a cytidine-containing compound, for example, one that includes cytidine or CDP; the cytidine-containing or cytosine-containing compound further includes choline (and is, for example, CDP-choline); the mammal being treated has a stimulant dependency or stimulant craving; and the mammal being treated is a pregnant woman or a child with antenatal exposure to a stimulant.

In another aspect, the invention features a method for treating cerebral vasoconstriction sequelae in a mammal, involving administering a therapeutically-effective amount of either a cytosine-containing or cytidine-containing compound to the mammal. In various preferred embodiments, the vasoconstriction is cocaine induced; the vasoconstriction is induced by a substance that causes vasoconstriction; the mammal is a human; the therapeutically effective compound is a cytidine-containing compound, for example, one that includes cytidine or CDP; and the cytidine-containing or cytosine-containing compound further includes choline (and is, for example, CDP-choline).

By "treating" is meant the medical management of a patient with the intent that a cure, amelioration, or prevention of a dependency or a relapse or associated disease, pathological condition, or disorder will result. This term includes active treatment, that is, treatment directed specifically toward improvement of the dependency or associated cure of a disease, pathological condition, or disorder, and also includes causal treatment, that is, treatment directed toward removal of the cause of the dependency or associated disease, pathological condition, or disorder. In addition, this term includes palliative treatment, that is, treatment designed for the relief of symptoms rather than the curing of the dependency, disease, pathological condition, or disorder; preventive treatment, that is, treatment directed to prevention of the dependency or associated disease, pathological condition, or disorder; and supportive treatment, that is, treatment employed to supplement another specific therapy directed toward the improvement of the dependency or associated disease, pathological condition, or disorder. The term "treating" also includes symptomatic treatment, that is, treatment directed toward constitutional symptoms of the dependency or an associated disease, pathological condition, or disorder.

By "exposure" and "exposed" is meant the condition of being subjected to a stimulant either inadvertently or intentionally. This term shall include any mechanism for introducing the stimulant to the mammal, the most typical being insufflation, inhalation, and intravenous administration. This term also includes exposure to a stimulant when presented in combination with other compounds not considered stimulants. The term exposure may also represent single or multiple incidents.

By "stimulant" is meant any substance that temporarily increases functional activity, and preferably cardiac, respiratory, cerebral, nervous, vascular, motor, or vasomotor functional activity. Preferred stimulants include, without limitation, cocaine, amphetamines, methamphetamine, and methylphenidate.

By "therapeutically-effective amount" is meant an amount of a cytidine-containing or cytosine-containing compound sufficient to produce a healing, curative, or ameliorative effect either in the treatment of a stimulant exposure or stimulant dependency.

By "cytidine-containing compound" is meant any compound that includes, as a component, cytidine, CMP, CDP, CTP, dCMP, dCDP, or dCTP. Preferred cytidine-containing compounds include, without limitation, CDP-choline and cytidine 5'-diphosphocholine frequently prepared as cytidine 5'-diphosphocholine [sodium salt] and also known as citicoline.

By "cytosine-containing compound" is meant any compound that includes, as a component, cytosine.

By "dependency" is meant any form of behavior that indicates an altered or reduced ability to make decisions resulting, at least in part, from the use of stimulants. Representative forms of dependency behavior may take the form of antisocial, inappropriate, or illegal behavior and include those behaviors directed at the desire, planning, acquiring, and use of stimulants. This term also includes the psychic craving for a drug that may or may not be accompanied by a physiological dependency, as well as a state in which there is a compulsion to take a drug, either continuously or periodically, in order to experience its psychic effects or to avoid the discomfort of its absence. Forms of "dependency" include habituation, that is, an emotional or psychological dependence on a compound to obtain relief from tension and emotional discomfort, as well as physical or physiological dependence, that is, use of a compound to prevent withdrawal symptoms.

By "antenatal exposure" is meant exposure of a subject to a stimulant before birth via the antepartal mother, the antepartal mother having had an exposure as described herein.

By "craving" is meant a behavior that reflects a consuming desire, longing, or yearning for a stimulant. This term may refer to aspects of behaviors that are components of a dependency.

By "cerebral vasoconstriction sequelae" is meant any condition following and resulting from the constriction of blood vessels in the cerebrum provoked by a motor nerve or chemical compound, for example, any disease, pathology, disorder, or dependency subsequent to stimulant exposure. This term includes cerebral ischemia, neuropathologies, neurological deficits, altered brain chemistry, reduced levels of task mastering, cognitive impairment, behavioral changes, vegetative responses, mental deterioration, altered conditioned avoidance and auditory response parameters, and motor activity impairment. Such conditions may be characterized by altered levels of phosphomonoesters (PME), phosphodiesters (PDE), phosphocreatine (PCr), nucleotide triphosphates (NTP), inorganic phosphorus (Pi), the PCr/Pi ratio, the $\beta$-NTP/PCr ratio, cerebral phosphorus metabolites, phospholipid precursors, cellular and organelle phospholipid synthesis, membrane synthesis, tyrosine hydroxylase activity, dopamine and dopamine metabolism, bioenergetic function, fatty acid release, neutral acids, phosphatidylcholine and glycerophospholipid degradation, glucose, pyruvate, acetylcholine, norepinephrine, vasodilation, synatopsomal phosphorylation, cellular proliferation, neuronal injury, edema, mitochondrial ATPase and $Na^+$-$K^+$ ATPase sensitivity, phospholipase $A_2$ activation, EEG parameters, cardiovascular and respiratory parameters. The term shall include any of the above conditions altered alone or in combination.

The present invention provides a number of advantages. Importantly, it provides one of the first therapeutics for the treatment of stimulant dependencies (such as cocaine dependencies). In addition, the cytidine-containing compounds utilized herein are relatively non-toxic, and CDP-choline, in particular, is pharmocokinetically understood and known to be well tolerated by mammals.

DETAILED DESCRIPTION OF THE INVENTION

The drawings will first briefly be described.

BRIEF DESCRIPTION OF THE DRAWINGS

FIG. 1 is diagram depicting a time line and the points at which various procedures were performed throughout the experimental protocol described herein.

FIG. 7 is a chart depicting the effects of cocaine on cardiovascular parameters such as heart rate (HR) and systolic (Sys) and diastolic (Dia) blood pressures.

FIG. 8 is a chart depicting the effects of cocaine on cerebral vasoconstriction as measured by magnetic resonance angiography (MRA).

FIG. 9 is a chart depicting percent differences in cerebral phosphorus metabolite profiles of patients on methadone maintenance (MM) as measured by phosphorus magnetic resonance spectroscopy.

Figure 2A:
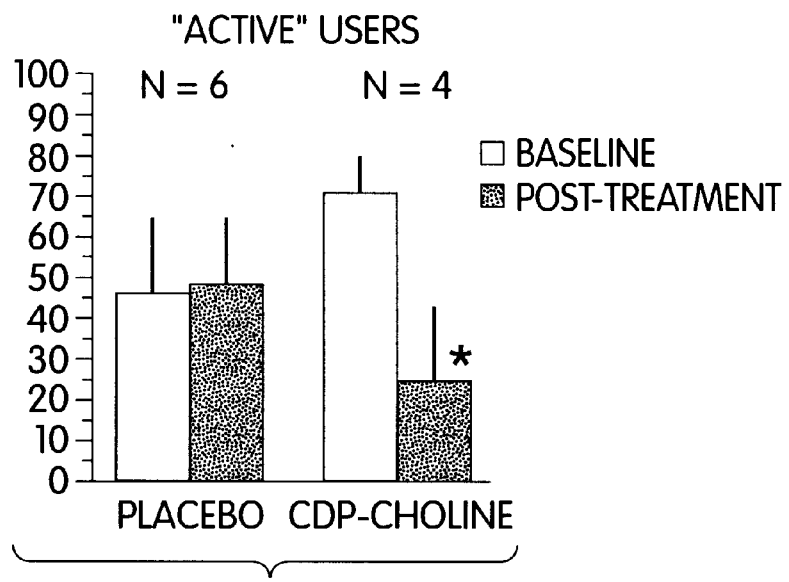
FIGS. 2A and 2B are histograms depicting changes in the likelihood to use cocaine in patients classified as "active" (FIG. 2A) versus "clean" (FIG. 2B) when treated with CDP-choline (*indicates significance at p<0.05 relative to baseline). The unshaded bars represent patients at baseline, and the shaded bars represent patients post-treatment. The y axis is a visual analog scale (VAS) in millimeters where 100 represents "most ever" and zero represents "not at all." The VAS is designed to quantitate subjective mood statements.

The invention described herein features a method for the treatment of stimulant abuse and its symptoms, as well as stimulant dependency and associated self-destructive behaviors. The invention focuses on cocaine abuse and addiction although other stimulant dependencies may be similarly treated. To this end, the invention features the use of cytidine-containing or cytosine-containing compounds to alleviate symptoms of abuse and dependency. One preferred cytidine-containing compound is CDP-choline (also referred to as citicoline or CDP choline [sodium salt]). As described herein, CDP-choline has been found to have two important therapeutic properties. First, CDP-choline improves brain chemistry in patients suffering from symptoms of cocaine abuse as a result of cocaine-induced cerebral vasoconstriction. And second, CDP-choline alleviates the dependency exhibited by active cocaine users.

In addition, the results described herein demonstrate that symptoms of cocaine abuse are very likely functions of cocaine-induced cerebral vasoconstriction. These results also demonstrate that symptoms of opiate abuse and dependency (specifically, heroin abuse and dependency) induce alterations in some, but not all, brain chemistry indices and that certain of those parameters in patients with heroin addictions are improved with methadone in a manner akin to improvements observed in patients with cocaine addictions treated with CDP-choline. The present invention therefore enables methods and reagents for the treatment of stimulant abuse, such as cocaine abuse, by providing original data from human trials.

The following detailed examples are provided for the purpose of illustrating, and not limiting, the invention.

EXAMPLE 1

CDP-Choline is an Effective Treatment for Cocaine Abuse and Dependence

A small double-blind clinical trial of CDP-choline versus placebo for altering cocaine craving and modifying responses to cocaine-related stimuli was conducted. A total of fourteen crack cocaine users were recruited by passing a psychiatric, medical, and clinical laboratory evaluation and provided informed consent to participate in this outpatient treatment study. The subjects were completely randomized and the resultant demographic profiles are shown in Table 1.

TABLE 1

Demographics of Study Population

| Variables | CDP-Choline* | Placebo |
|---|---|---|
| # of Subjects | 6 | 8 |
| Race (Cau/Afr Amer) | 2/4 | 4/4 |
| Active Users | 4 | 6 |
| Clean 6–12 months | 2 | 2 |
| Age | 38.0 ± 6.1 | 35.8 ± 8.5 |
| Weight (kg) | 70.4 ± 6.5 | 86.7 ± 12.9 |
| Sex (M/F) | 4/2 | 7/1 |
| Cocaine Use (yr) | 9.8 ± 4.2 | 11.6 ± 3.9 |
| Cocaine Use (#/week) | 10.0 ± 10.0 | 7.2 ± 1.6 |
| Ethanol Use (yr) | 20.8 ± 6.9 | 18.4 ± 7.2 |
| Ethanol Use (#/week) | 13.0 ± 8.5 | 11.0 ± 4.7 |

*500 mg oral dose twice daily

The subjects participated in two evaluation sessions, each separated by two weeks, during which subjects received either placebo or CDP-choline (500 mg, twice daily). Frequent assessments for adverse effects and urine screens were performed during treatment. The overall research design is depicted in FIG. 1.

On each of two assessments sessions, subjects were required to report to the laboratory to fill out a number of subjective mood state questionnaires. After this initial assessment, subjects then sat in a sound- and light-attenuated room and were prepared for standard EEG/ERP recording and physiological monitoring. After a 1 hour baseline period the first of three videos was shown. Subsequent videos were shown at 1 hour intervals. The three videos included: (1) a neutral tape of coral sea life; (2) an emotionally laden footage of the movie "An American Werewolf in London;" and (3) footage of two men buying, preparing, and smoking crack cocaine. Continuous physiologic and electrophysiologic brain mapping measures were made before and after each videotape.

In addition, subjects were required to answer a series of questionnaires that were designed to assess the subject's degree of cocaine craving. These included questions like; "What is the likelihood of your using cocaine?;" "Are you planning to use cocaine?;" and "How much do you desire to use cocaine?"

Finally, a test battery for reaction time and psychomotor function was given. The CalCAP® is a series of 10 different tasks each becoming more difficult as the test proceeds.

Safety Assessments

The results of the assessments for adverse reactions revealed that CDP-choline not only had no side effects, but subjects were unable to detect whether they had received an active or placebo dose. No changes in health status or blood or urine chemistry analyses were observed. At baseline, three subjects in the placebo group and one in the CDP-choline group had nonclinical sinus bradycardia. One subject who received CDP-choline, developed a mild, non-relevant increase in the cardiac P-R interval. Finally, there were no changes in heart rate or blood pressure.

Population Dynamics

A post-hoc analysis revealed that both the placebo and CDP-choline group contained two distinct populations of crack cocaine users. "Active" users were defined as those who were currently using cocaine at the time of recruitment. These reports were confirmed using urine drug screens. "Clean" users were those who had been cocaine-free for the past 6–12 months. The distribution of active and clean users is depicted in Table 2.

TABLE 2

Distribution of "Active" versus "Clean" Users in the Study Population

| | Treatment | |
|---|---|---|
| Status | CDP-choline | Placebo |
| Active | 4 | 6 |
| Clean | 2 | 2 |

This distinction appeared to be very important in characterizing the efficacy of CDP-choline.

Assessment of Cocaine Dependency/Craving

Figure 2B:
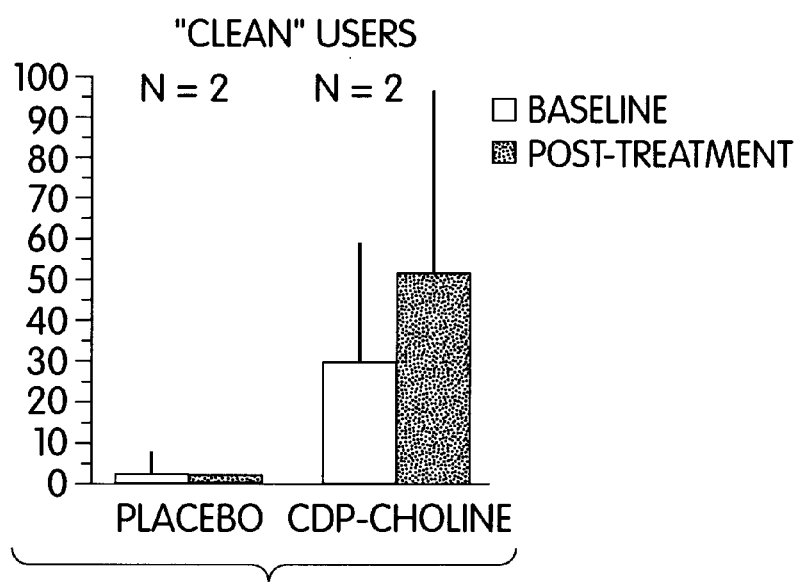

Responses to the Pre-Questionnaires with respect to "Likelihood to use cocaine" revealed a statistically significant decrease in this variable in the active cocaine users who had been treated with CDP-choline as compared to those patients treated with a placebo (FIGS. 2A and 2B).

Figure 3A:
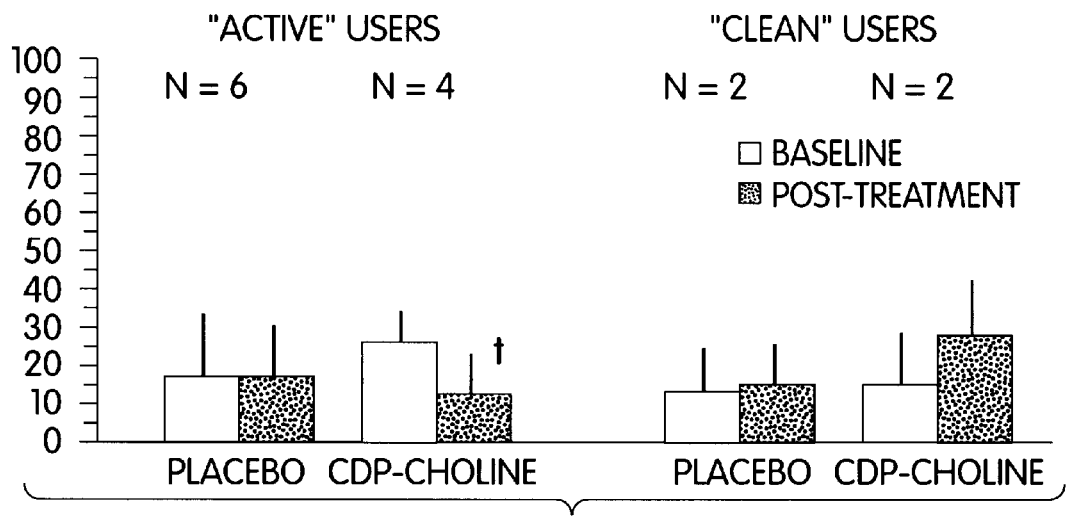
FIGS. 3A and 3B are histograms depicting changes in the percent levels of cocaine craving exhibited by patients when treated with CDP-choline († indicates a trend relative to baseline). The unshaded bars represent patients at baseline, and the shaded bars represent patients post-treatment. The scale is the same as described in FIG. 2A and 2B.
Figure 3B:
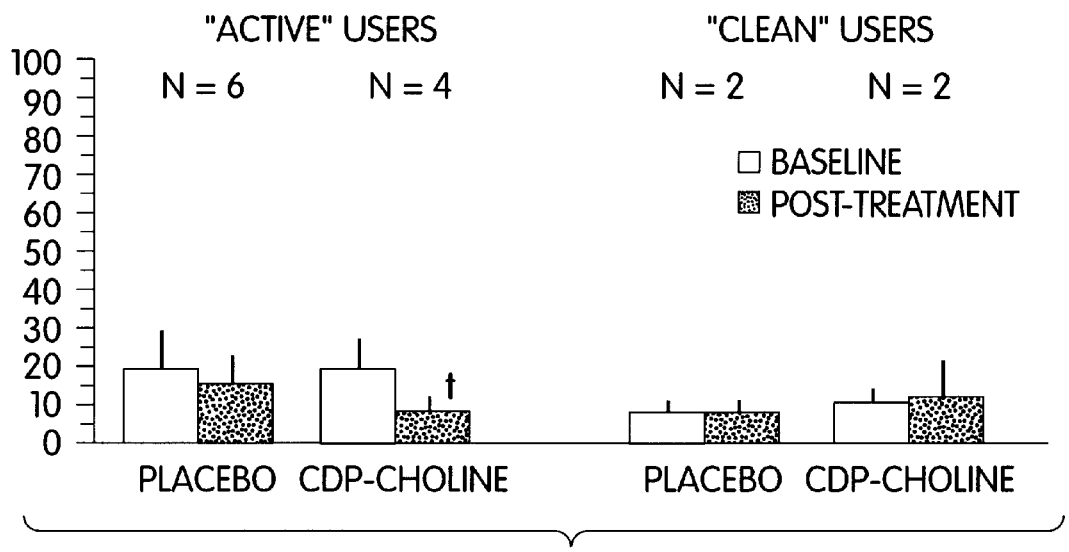

As another measure of whether treatment with CDP-choline could decrease cocaine dependency in "active" versus "clean" users, patients were queried on the probability of their "planning to use cocaine" and their "desire to use cocaine" (FIGS. 3A and 3B ). Although not statistically significant, there were strong trends (p=0.06–0.08) for reductions in these parameters in "active" users. A similar reduction in the "likelihood to use" question was observed even after patients were subjected to the video depicting crack cocaine use (data not shown).

Figure 4:
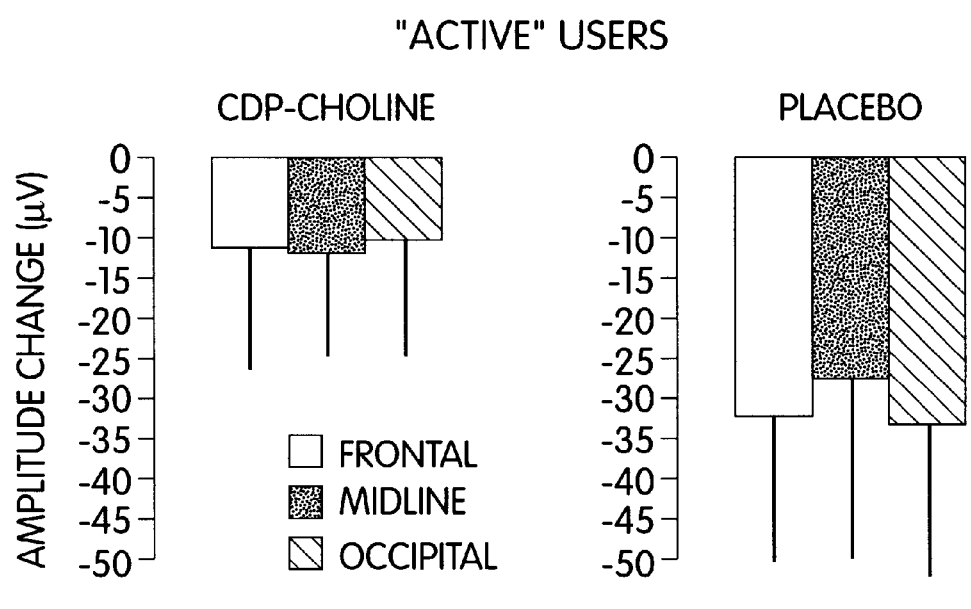
FIG. 4 is a histogram depicting improved cognitive processing ability in patients who are "active" users treated with CDP-choline as measured in the P300 ERP test.

To test for the ability of CDP-choline to improve cognitive function in cocaine users, a P300 ERP test was performed on "active users" (FIG. 4). The P300 ERP test is a measure of memory encoding performance during the assessment of a novel stimulus. Reductions in amplitude are generally interpreted as reflecting reduced cognitive processing. FIG. 4 shows that (compared to baseline) the reduction in P300 amplitude was modest and insignificant in the CDP-choline treated "active" users while the reduction in placebo-treated "active" users was significantly greater.

Figure 5:
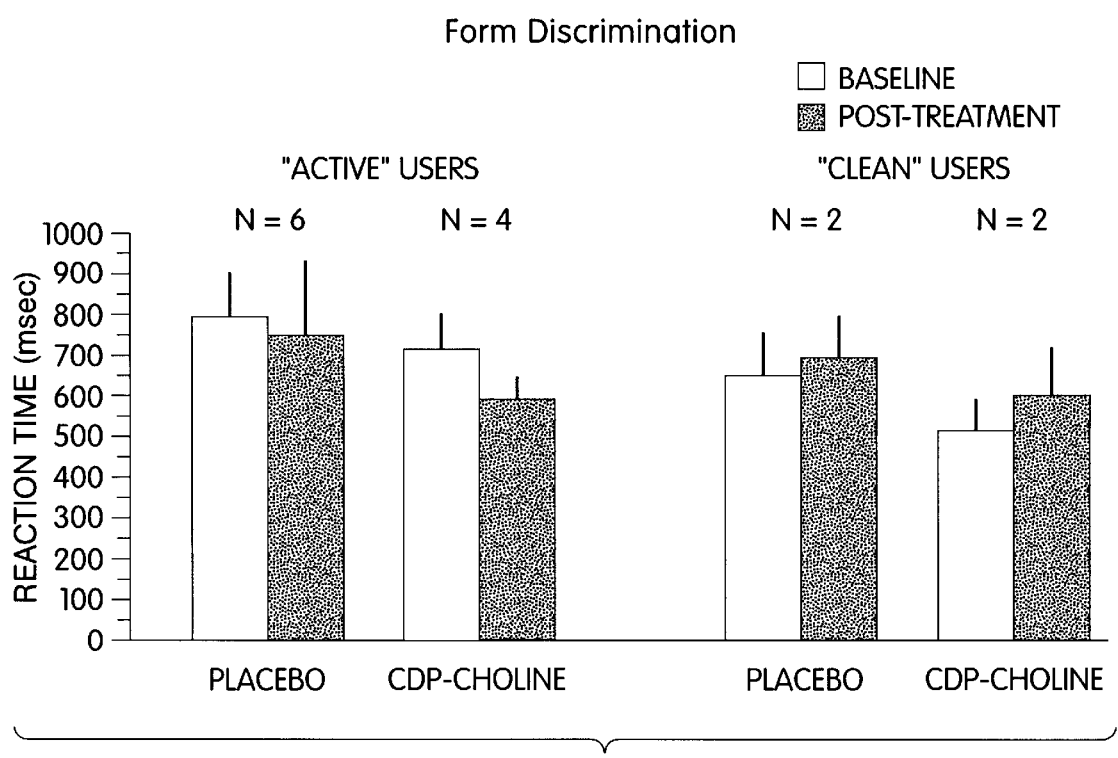
FIG. 5 is a histogram depicting iconic memory performance in patients classified as "active" when treated with CDP-choline. The unshaded bars represent patients at baseline, and the shaded bars represent patients post-treatment.
Figures 6A, 6B:
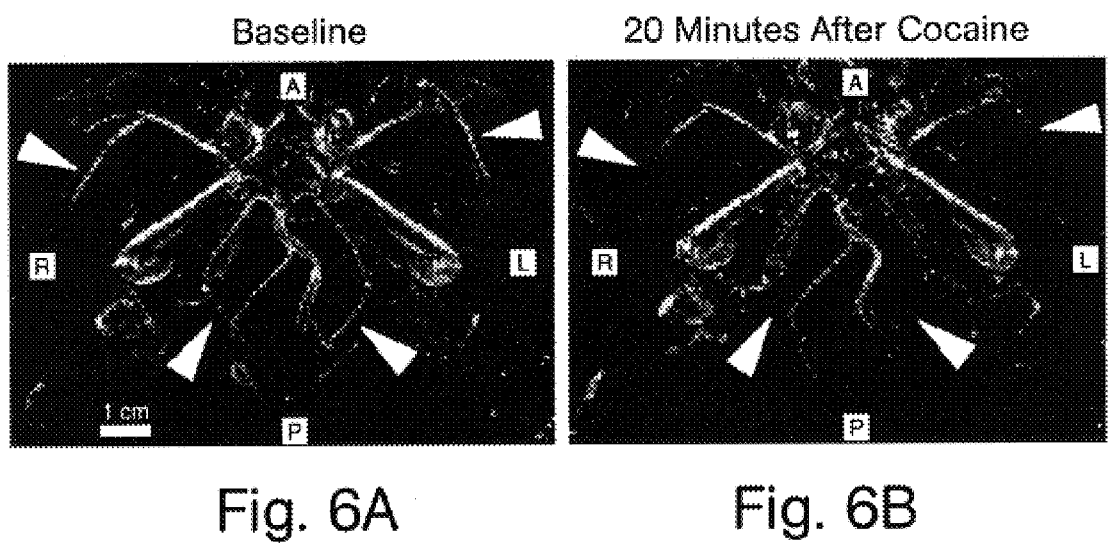
FIGS. 6A and 6B are Magnetic Resonance Images (MRI) depicting marked cerebral vasoconstriction following intravenous cocaine administration. Axial maximum intensity projection images are indicated at baseline (FIG. 6A) and 20 minutes following intravenous cocaine (0.4 mg/kg) administration (FIG. 6B). Cocaine induced a signal loss at distal segments of the middle cerebral arteries (upper arrowheads) and in the posterior cerebral arteries (lower arrowheads), indicative of vasoconstriction. A=anterior, P=posterior, L=left, and R=right.

To further test for the ability of CDP-choline to improve or cognitive function in cocaine users, patients treated or untreated with CDP-choline were tested for their ability to discriminate forms using the CalCAP® test (FIG. 6). Form discrimination was measured by showing the subjects 3 geometric shapes simultaneously and asking them to press a key when two were identical in shape and color. This task required that the subjects make rapid comparisons and measured their ability to retain iconic memory. Patients classified as "active" users who were treated with CDP-choline showed a trend toward significant improvement in their reaction time (145 msec) in Form Discrimination as compared to untreated "active" users (FIG. 5).

Summary of Human Clinical Trial Results

In this human trial designed to test the effectiveness of CDP-choline in the treatment of cocaine abuse and dependency, the following observations were made:

1. CDP-choline improved short term memory and cognitive function in patients with a cocaine exposure.
2. Patients with a cocaine dependency or craving were benefitted by treatment with CDP-choline.
3. CDP-choline is nontoxic, well-tolerated, and was undetectable by the subjects.

These results indicate that CDP-choline is a useful adjunct to current therapies for cocaine abuse, particularly in individuals who are currently active users. Without being bound to a particular theory, these results are likely due to CDP-choline's weak dopamine agonist activity. In addition, these results indicate that, because of its low toxicity, CDP-choline may be useful for treating pregnant women, adolescents, and babies born to cocaine-dependent women. This last group is of particular importance because CDP-choline's ability to reduce stroke symptoms suggests that this therapeutic may also reverse many of the detrimental micro-infarcts that occur during in utero exposure to cocaine.

To date, there are no approved pharmacotherapies for cocaine abuse or dependence. Administering CDP-choline therapeutically therefore provides an important approach to minimizing the detrimental effects of cocaine abuse and dependency and to speeding the recovery process.

In addition, based on CDP-choline's mechanism of action, this and other cytidine-containing or cytosine-containing compounds are generally useful for the treatment of other types of stimulant abuse and dependence, including, but not limited to, amphetamine, methamphetamine, and methylphenidate abuse and dependence.

EXAMPLE 2

Cocaine-Induced Cerebral Vasoconstriction in Humans

This clinical study was designed to evaluate whether intravenous administration of low doses of pure, pharmaceutical grade cocaine hydrochloride could induce cerebral vasoconstriction in otherwise healthy human subjects. Serial noninvasive imaging of the major cerebral arteries was conducted at baseline and twenty minutes following cocaine administration, using magnetic resonance angiography (MRA). MRA is highly sensitive to blood flow perturbations. Vasoconstriction results in vessel signal intensity loss at the site of and distal to the constricted region, and MRA has proven useful for detecting acute cerebral vasospasm. This technique is noninvasive and does not utilize ionizing radiation, facilitating within-subject repeated-measure study designs.

Subjects

Subjects with either no history of cocaine use or with a diagnosis of cocaine abuse or dependence were excluded from this study. A group of 24 healthy, medically and neurologically normal males aged 29±5 years (mean±SD) who reported casual cocaine use (median=8, range =3 to greater than 40 lifetime exposures, primarily via insufflation) was selected for study participation. Subjects provided written Informed Consent with McLean Hospital Institutional Review Board approval. Subjects underwent a complete physical and neurological exam including ECG and hematology prior to study, and provided a medical history including estimates of illicit drug usage. On the study day, subjects provided breath and urine samples to detect recent alcohol or illicit drug use. Breath samples were analyzed with an Alco Sensor III Breathalyzer (Intoximeters Inc., St. Louis, Mo.). Urine samples were analyzed for the presence of cocaine, amphetamines, phencyclidine, opiates, barbiturates, benzodiazepines, and tetrahydrocannabinol with a Triage™ Test (Biosite Diagnostics, San Diego, Calif.). All subjects had negative breath alcohol samples and urine screens. Each subject had an 18G angiocath inserted in a vein overlying the antecubital fossa for cocaine or placebo administration. Subjects were fitted with noninvasive cardiovascular monitoring equipment (In Vivo Research, Inc., Orlando, Fl.) including 4 lead electrocardiogram (ECG), blood pressure cuff, and pulse oximeter, to provide continuous monitoring of ECG, blood pressure, and heart rate.

Magnetic Resonance Scanning

Magnetic resonance imaging was conducted with a 1.5 Tesla Signa Scanner (General Electric, Milwaukee, Wis.). T1 weighted sagittal localizer images (TE/TR: 19/600 msec) were used to position MRA imaging sets. Angiogram imaging sets of 60 axial images were collected with the three dimensional Time of Flight (3D TOF) magnetization transfer imaging option with flow compensation and saturation. The following acquisition parameters were used: TE/TR: 35/20 msec, FOV: 19 cm, matrix: 256×192, slice thickness: 1.2 mm, 1 NEX, imaging time: 7.5 minutes. Each image set produced a single axial maximum intensity projection (MIP) image which was analyzed for drug effects. Cocaine (0.2 or 0.4 mg/kg) or placebo was then administered by slow intravenous injection over 1 minute; all doses were given in a double-blind manner. Seventeen minutes after drug administration, a post-drug 3D TOF series was initiated, with a midpoint of the imaging sequence occurring 20 minutes after drug administration.

Image Analysis

Baseline and post cocaine/placebo axial MIP images from each subject were analyzed for drug-induced changes. Two expert raters, blinded with regard to study drug administration, independently analyzed the 24 image sets. Prior to analysis, the 2 raters agreed on criteria that would be used to determine alterations between baseline and post-drug images. Subtle image differences discernible by both raters, including change in the caliber of moderate and large sized arteries and focal narrowing or complete signal loss in a major arterial structure were considered as alterations. Image sets were scored as unchanged, ambiguous, or altered. Concordance was established when both raters agreed in their independent scan ratings. A weighted kappa statistic of 0.64 for interrater agreement showed a very high degree of between-rater concordance (p=0.002, two-sided; unweighted kappa=0.70, p<0.0001) (Fleiss, J L, et al, Educ. Psychol. Meas., 33:613–619, 1973).

Results of Study on Cocaine-Induced Cerebral Vasoconstriction

Baseline cardiovascular parameters were normal in all subjects, with heart rate (HR) averaging 68±2 bpm (mean±SE), and systolic (Sys) and diastolic (Dias) blood pressures averaging 126±3 and 70±3 mm Hg, respectively (FIG. 7). Slight increases in HR, Sys, and Dias were observed in the placebo-administered group (FIG. 7) and were attributed to expectancy effects. Both cocaine doses elevated heart rate for the duration of the experiment, with peak increases in HR, Sys, and Dias (FIG. 7) occurring approximately 6–10 minutes following drug administration. Twenty minutes after cocaine or placebo administration, at the midpoint of the MRA acquisition, HR and Dias remained elevated in all subjects administered cocaine and Sys remained elevated in subjects administered 0.4 mg/kg cocaine (FIG. 7). An overall dose effect of cocaine (repeated measures ANOVA) was detected for HR and Dias at the 20 minute time point (FIG. 7).

Image analysis revealed a relationship between cocaine administration and angiographic alteration. All baseline images were judged to be normal. Raters determined that 5 of 8 subjects who received 0.4 mg/kg cocaine experienced angiographic alterations indicative of cerebral vasoconstriction. These ranged from subtle differences in arterial caliber to more significant alterations, including focal narrowing or complete signal loss from a major arterial structure. These alterations were detected in the posterior cerebral artery, the middle cerebral arteries (FIG. 6), vertebral arteries, and the anterior and posterior communicating arteries. Three of 9 subjects who received 0.2 mg/kg cocaine had angiographic alterations in several arteries including the anterior communicating arteries and the posterior and middle cerebral arteries. One of 7 subjects who received placebo was ruled to have an altered post-placebo MRA scan. FIG. 8 shows the observed classification of angiogram results stratified by cocaine dosage for all image sets. Statistical analysis of concordantly rated scans using a linear-by-linear association model (Agresti, A, Categorical Data Analysis. John Wiley & Sons, New York, 1990) for the ordered categories of 0=unchanged, 1=ambiguous, and 2=altered, indicated a significant association of increasing prevalence of altered scans with increasing cocaine dose (p=0.041, one-sided). When discordantly rated scans were included, the significance of the association decreased slightly (p=0.056). These findings demonstrated an apparent relationship between cocaine administration and altered MRA scan; moreover, this effect appeared to be dose-related. A stratified analysis of this small sample by frequency of self-reported lifetime cocaine use (1–10 times, 11–40 times, or greater than 40 times) revealed a statistically stronger dose-response relationship (p<0.001), suggesting that prior cocaine use may have a cumulative effect in promoting angiographic changes indicative of vasoconstriction.

The study design precluded direct measurement of plasma cocaine levels in the present study population. However, we obtained plasma cocaine levels by gas chromatographic analysis (Teoh, S K et al., J. Clin. Psychopharmacology 13:87–99, 1993) from comparable subjects administered cocaine by identical protocols. Peak plasma cocaine levels of 230±10 and 90±10 ng/ml were found 6–8 minutes following intravenous administration of 0.4 (n=3) and 0.2 (n=6) mg/kg doses of cocaine, respectively. Plasma cocaine levels of 180±30 and 80±10 ng/ml were found at 20 minutes post-administration, corresponding to the midpoint time of the present MRA acquisition, following 0.4 and 0.2 mg/kg cocaine doses, respectively. These values and their course closely parallel those published in a recent report of the venous plasma cocaine level time course following intravenous cocaine administration (Evans, S M et al, J. Pharmacol. Exper. Therap. 279:1345–1356, 1996).

Summary of Results

The above results are the first to document that intravenous administration of a relatively low dose of cocaine to otherwise healthy humans can induce angiographic changes indicative of cerebral vasoconstriction. This finding suggests that low cocaine doses are sufficient to induce cerebrovascular dysfunction. The data also reflects a dose-effect relationship between cocaine and vasoconstriction. This finding suggests that moderate to heavy cocaine users, who may attain plasma cocaine levels greatly exceeding those likely to have been achieved in this study, may experience a higher incidence of cerebral vasoconstriction. As cerebral vasoconstriction has been linked to hypoperfusion and persistent hypoperfusion has been associated with neuronal dysfunction, the present findings indicate that moderate to heavy cocaine use is likely associated with neuronal damage.

Cumulative Effects of Cocaine and the Etiology of Chronic Cocaine-Induced Brain Dysfunction Although it is assumed that chronic cocaine abuse is requisite to produce persistent perfusion defects and cognitive dysfunction, it is presently unclear what threshold level of cocaine exposure results in these conditions. The cognitive dysfunction observed in chronic cocaine abusers is related to amount of cocaine used, suggesting a cumulative effect of cocaine on brain function. The present study documents a relationship between prior cocaine use and the propensity to experience vasoconstriction, suggesting that cocaine may have a cumulative effect in producing cerebrovascular dysfunction in addition to its acute vasoconstrictive effect. In this regard, self-reported lifetime cocaine use of more than 10 times nearly doubled the risk for experiencing a cocaine-induced angiographic change (75%) compared to the risk experienced by subjects reporting 10 or fewer episodes of lifetime cocaine use (38%). The present data suggest that the incidence of cocaine-induced cerebral vasoconstriction may be increased in individuals who escalate from experimental to casual or recreational cocaine use.

The present study was conducted at a single time point following cocaine administration, precluding analysis of the time-dependence of cocaine-induced vasoconstriction. Because cocaine-induced vasoconstriction is a transient phenomenon and because our time frame for its detection was short, it is conceivable that more subjects experienced vasoconstriction than detected in the current study. Additionally, we are unable to address whether cocaine or its metabolites, some of which are potent vasoconstrictors, mediate vasoconstriction. Cocaine metabolites may play an important role in inducing delayed cerebral vasoconstriction, because their levels gradually increase over several hours and in extreme cases persist for up to several weeks. Thus they may trigger prolonged cerebral vasoconstriction associated with decreased cerebral perfusion.

The present study used intravenous cocaine administration as the drug delivery method, while intranasal administration and smoking of the alkaloidal form "crack" are the more common forms of administration. The mode of cocaine administration has been suggested to be related to cerebrovascular effect, with the intravenous route leading to hemorrhagic strokes and "crack" smoking leading to both ischemic and hemorrhagic stroke. Thus, it is possible that different forms of cocaine or different routes of administration may produce dissimilar rates or severity of vasoconstriction. However, our finding of a dose-effect relationship between cocaine and vasoconstriction suggests that once a sufficient plasma cocaine concentration is achieved, cerebral vasoconstriction likely occurs.

Moreover, the results of this clinical trial demonstrate a real and substantial dose-effect relationship between cocaine and cerebral vasoconstriction. These results underscore the risks of single doses of cocaine in promoting cerebrovascular abnormalities, particularly in individuals with other risk factors. The data also strongly suggest that there is an increased risk of cerebrovascular dysfunction in individuals who are frequent or chronic cocaine users, and that this dysfunction may be progressive. Together, these findings highlight the potential dangers of cocaine use on cerebrovascular function and document the importance of cytosine-containing or cytidine-containing treatments such as CDP-choline that protect against or correct vasoconstriction or its symptoms.

EXAMPLE 3

Cerebral Phosphorus Metabolism in Heroin-Dependent Polydrug Abusers During Methadone Maintenance Heroin abusers have cerebral metabolic and perfusion abnormalities that persist beyond the period of drug intoxication and acute withdrawal (London, ED, et al. Res. Comm. Subst. Abuse 10:141–144, 1989; Rose, J S et al, Psychiatry Research: Neuroimaging 67:39–47, 1996). A number of opiates, including candidates for the treatment of opiate abuse, have been evaluated for their effects on brain function (London, E D, et al. Res. Comm. Subst. Abuse 10:141–144, 1989; London, E D et al, Arch. Gen. Psychiatry 47:73–81, 1990; Walsh, S L et al, Neuropsychopharmacology 10:157–170, 1994). However, no study to date has examined the neurochemical effects of the most widely utilized intervention for the treatment of opiate abuse, methadone. Methadone has demonstrated efficacy in improving psychiatric symptoms and overall health in opiate abusers (McLellan, A T et al, JAMA 247:1423–1428, 1982; Ball, J C et al, The effectiveness of methadone maintenance treatment: Patients, programs, services, and outcome. New York, Springer-Verlag, 1991). However, it is unknown whether these clinical improvements are related to improved cerebral function. Consequently, the present study was conducted in heroin-dependent polydrug abusers chronically treated with methadone, to evaluate indices of cerebral biochemistry using phosphorus magnetic resonance spectroscopy ($^{31}$P MRS). $^{31}$P MRS allows noninvasive measurement of brain membrane integrity and bioenergetic status.

To carry out this clinical study, heroin-dependent polydrug abusers (9 females and 6 males, aged 40±4 years, mean±SD) were recruited from an outpatient methadone maintenance (MM) clinic. Potential subjects with a history of alcohol abuse or HIV infection were excluded from the study. This population was subdivided into two groups based on MM treatment duration: the short-term group (n=7, 40±24 weeks) and the long-term group (n=8, 137±53 weeks). The methadone dose administered to these subjects was in the range of 60–80 mg per day and was statistically equivalent in the two MM treatment duration groups. All medical histories, including random biweekly urine toxicology testing throughout the course of methadone maintenance therapy, were reviewed in order to determine study population demographics. Positive urine tests for the following substances were found greater than 10% of the time: methadone-98%; benzodiazepines-39%; opiates-37%; cocaine-18%. Clean urine screens were found 26% of the time. These frequencies were statistically equivalent across MM duration subgroups.

An age matched comparison group (6 females and 10 males, aged 40±4 years) with no history of substance abuse or neurological or psychiatric disorder was studied with identical procedures. All subjects provided written informed consent with McLean Hospital Institutional Review Board of Approval.

All subjects provided breath and urine samples immediately prior to scanning to determine whether recent alcohol or illicit drug use had occurred. Breath samples were analyzed with an Alco Sensor III Breathalyzer (Intoximeters Inc., St. Louis, Mo.). A positive breath alcohol sample was grounds for study exclusion. Urine samples were analyzed for the presence of illicit drugs with a Triage™ Test (Biosite Diagnostics, San Diego, Calif.). A positive urine test for illicit drug use was not grounds for exclusion in the MM population as it was assumed that this group would have ongoing drug use. The frequency of positive Triage testing for all substances was statistically equivalent across MM duration subgroups.

Imaging

Spectra were acquired on a 1.5 Tesla General Electric Signa Scanner using a doubly-tuned, linear proton, quadrature phosphorus head coil. An axial whole brain slice volume of 50 mm thickness was prescribed through the orbitofrontal/occipital cortices as described (Christensen, J D et al, Magn. Reson. Med. 35:658–663, 1996).

Spectra were processed with VARPRO/MRUI (van den Boogaart, A et al, NMR Biomed. 8:87–93, 1995). A 5 Hz exponential line broadening filter was applied, and 7 peaks were fit to gaussian lineshapes by automated fitting: phosphomonoesters (PME), inorganic phosphorus (Pi), phosphodiesters (PDE), phoshocreatine (PCr), and γ-, α-, and β-nucleoside phosphates. The total phosphorus signal (summation of all peak areas) was statistically equivalent across groups allowing use of the % metabolite measure, the ratio of the area of each metabolite peak divided by the total phosphorus area, for between-group comparisons (Klunk, W et al, Neurobiol. Aging 15:133–140, 1994). Statistical analyses were performed using unpaired two-sided t-tests.

Results

The mole percentages of PME and PDE were significantly higher and the mole percent PCr was significantly reduced in the MM population (FIG. 9). When stratified into the short- and long-term MM treatment subgroups, different profiles of cerebral phosphorus metabolite abnormalities emerged. The short-term MM group had elevated % PME, % PDE, and β-NTP/PCr ratio, and reduced % PCr, % NTP, and PCr/Pi ratio. In contrast, the long-term MM group differed from the healthy comparison group only in having reduced % PCr levels. This group differed from the short-term MM group having higher % PCr levels and lower % PDE levels (FIG. 9).

Summary

The above findings indicated elevated PME and PDE as well as decreased PCr levels in heroin-dependent polydrug abusers. This may reflect membrane dysfunction and oxidative metabolism impairment secondary to perfusion defects. The metabolite profile is unique compared to findings in cocaine abusers in whom only PME and PDE elevations were noted and in cocaine-dependent polydrug abusers in whom elevated PME and decreased β-NTP levels were found. This suggests that polydrug abuse populations with different primary substance abuse patterns may have discrete phosphorus metabolite profiles.

The present data are quite interesting in that they also document an apparent normalization of most cerebral phosphorus metabolites in subjects who have undergone prolonged MM therapy. In this regard, only PCr levels were abnormal in the long-term MM group; PCr and PDE levels were significantly higher and lower (more normal) in this versus the short-term MM group. This apparent improvement is consistent with a prior study documenting improved cerebral perfusion in short-term abstinence from heroin abuse (Rose, J S et al, Psychiatry Research: Neuroimaging 67:39–47, 1996). What is further encouraging from the present data is that metabolite improvements were noted in subjects with ongoing illicit substance use (opiate positive urines nearly 40% of the time). This indicates that abstinence is not required for normalization of certain aspects of brain function. Together, the present findings suggest that cerebral phosphorus metabolites are useful markers of brain health and treatment efficacy in individuals with a polydrug abuse history. As also indicated by the above study, certain aspects of altered phosphorus metabolism in heroin addicts are unique compared to findings in cocaine abusers. Other aspects of this altered metabolism, such as membrane dysfunction and oxidative metabolism impairment secondary to perfusion defects, are common to both drug abusers and may therefore be treatable with cytosine-containing or cytidine-containing compounds, such as CDP-choline.

EXAMPLE 4

Cytidine-Containing and Cytosine-Containing Compounds

Figure 10:
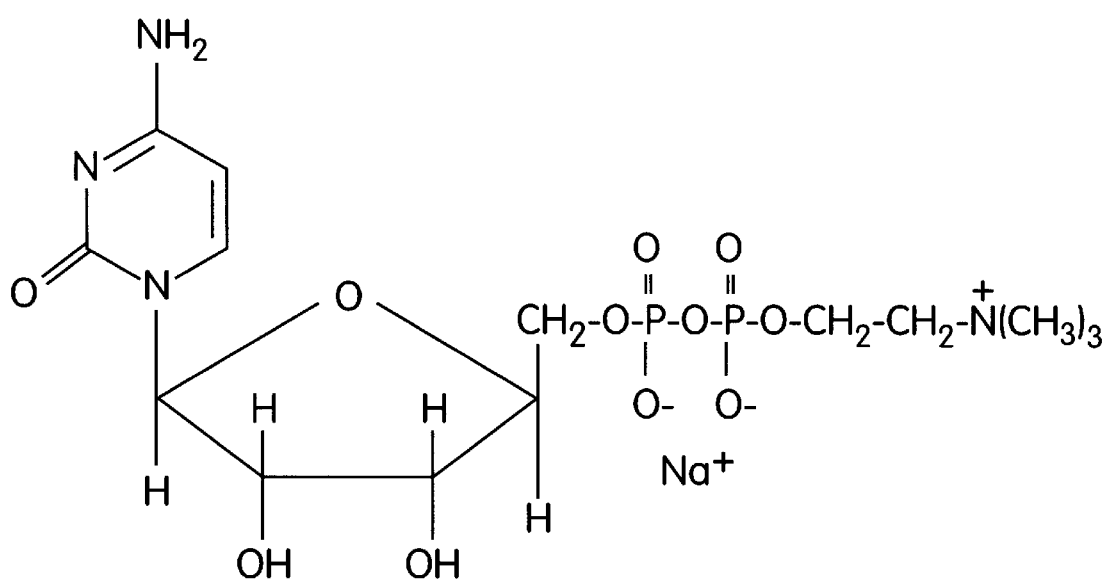
FIG. 10 is a depiction of the molecular structure of CDP-choline [sodium salt], also known as citicoline.

The human trials described herein made exclusive use of the cytidine-containing compound, CDP-choline, also known as citicoline, received from Interneuron Pharmaceuticals Inc. Nonetheless, because the cytidine moiety of this compound is responsible for the beneficial effects observed in these trials, any of a variety of cytidine-containing or cytosine-containing compounds are suitable for the treatment of the afflictions described herein. Examples of useful cytidine-containing or cytosine-containing compounds may include any compound comprising one of the following: cytosine, cytidine, CMP, CDP, CTP, dCMP, dCDP, and dCTP. Preferred cytidine-containing compounds include CDP-choline and cytidine 5'-diphosphocholine [sodium salt]. The above list of cytidine-containing and cytosine-containing compounds is provided to illustrate, rather than to limit the invention, and the compounds described above are commercially available, for example, from Sigma Chemical Company (St. Louis, Mo.). The molecular structure of CDP-choline [sodium salt] is provided in FIG. 10.

As noted above, one particular source of CDP-choline is Interneuron Pharmaceutical, Inc. The compound obtained from this source has the following characteristics:

Chemical Formula: $C_{14}H_{25}N_4O_{11}P_2Na$

Molecular Weight: 510.31

Physical and Chemical Characteristics: completely soluble in water as a 10% solution; practically insoluble in 100% ethanol.

The pH in water is between 6.5–7.5.

An available clinical dosage form of CDP-choline for oral administration is a 500 mg oblong tablet. Each tablet contains 522.5 mg CDP-choline sodium, equivalent to 500 mg of CDP-choline. Matching placebo tablets are also available. The excipients contained in both active and placebo tablets are talc, magnesium stearate, colloidal silicon dioxide, hydrogenated castor oil, sodium carboxy-methylcellulose, and microcrystalline cellulose.

CDP-choline is a naturally occurring compound that is synthesized from cytidine-5'-triphosphate and phosphocholine with accompanying production of inorganic pyrophosphate in a reversible reaction catalyzed by the enzyme CTP:phosphocholine cytidylyltransferase (Weiss, Metabolism and Actions of CDP-choline as an Exogenous Compound and Administered Exogenously as Citicholine, Life Sciences 56:637–660, 1995).

EXAMPLE 5

Administration of Cytidine-Containing and Cytosine-Containing Compounds

Cytidine-containing and cytosine-containing compounds, such as CDP-choline, are naturally occurring endogenous compounds. CDP-choline itself is synthesized in a sodium salt form for clinical use (see FIG. 10). One clinical dosage form for oral administration is a 500 mg oblong tablet. Each tablet contains 522.5 mg of CDP-choline sodium, equivalent to 500 mg of CDP-choline. For easier administration, such tablets may be cut into smaller pieces or crushed. Preferably, cytosine-containing and cytidine-containing compounds, such as CDP-choline, are administered at a dosage of at least 500 mg twice daily by oral administration.

Orally administered CDP-choline is bioavailable, with more than 99% of CDP-choline and/or its metabolites absorbed and less than 1% excreted in feces. CDP-choline, administered either orally or intravenously, is rapidly converted into the two major circulating metabolites, choline and cytidine. Major excretion routes are lung (12.9%) and urine (2.4%); the rest of the dose (83.9%) is apparently metabolized and retained in tissues.

Other formulations for treatment or prevention of the conditions described herein, may take the form of a cytosine-containing or cytidine-containing compound, such as CDP-choline, combined with a pharmaceutically-acceptable diluent, carrier, stabilizer, or excipient. Conventional pharmaceutical practice is employed to provide suitable formulations or compositions to administer such compositions to patients. Oral administration is preferred, but any other appropriate route of administration may be employed, for example, parenteral, intravenous, subcutaneous, intramuscular, intracranial, intraorbital, ophthalmic, intraventricular, intracapsular, intraspinal, intracisternal, intraperitoneal, intranasal, or aerosol administration. Therapeutic formulations may be in the form of liquid solutions or suspensions (as, for example, for intravenous administration); for oral administration, formulations may be in the form of liquids, tablets, or capsules; and for intranasal formulations, in the form of powders, nasal drops, or aerosols.

Methods well known in the art for making formulations are described, for example, in "Remington's Pharmaceutical Sciences," Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes.

If desired, slow release or extended release delivery systems may be utilized. Biocompatible, biodegradable lactide polymer, lactide/glycolide copolymer, or polyoxyethylene-polyoxypropylene copolymers may be used to control the release of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

In general, cytosine-containing or cytidine-containing compounds, such as CDP-choline, are administered at a dosage appropriate to the effect to be achieved and are typically administered in unit dosage form. As noted above, the preferred route of administration for most indications is oral.

An effective quantity of a cytidine-containing or cytosine-containing compound is employed to treat the conditions described herein. The exact dosage of the compound may be dependent, for example, upon the age and weight of the recipient, the route of administration, and the severity and nature of the symptoms to be treated. In general, the dosage selected should be sufficient to prevent, ameliorate, or treat the condition, or one or more symptoms thereof, without producing significant toxic or undesirable side effects.

In the case of CDP-choline, there have been no reported cases of overdoses. CDP-choline toxicity is largely self-limiting, ingestion of large amounts in preclinical studies shows common cholinergic symptoms (salivation, lacrimation, urination, defecation, and vomiting).

Other Embodiments

Preferably, cytidine-containing and cytosine-containing compounds as described herein are used for the treatment of human patients, but may also be used to treat any other mammal, for example, any pet or domesticated livestock. Any cognitive or behavioral problems associated with the types of altered brain chemistry described herein may be improved with cytidine-containing or cytosine-containing compounds, such as CDP-choline.

In addition, normal brain chemistry may also be enhanced by the administration of cytidine-containing or cytosine-containing compounds, with improvements in cognitive performance being the result.

For any of these additional uses, the cytidine-containing or cytosine-containing compound is administered by the general methods described herein.

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth, and follows in the scope of the appended claims.

Other embodiments are within the claims.

What is claimed is:

1. A method of treating a mammal exposed to a stimulant, comprising administering to said mammal a therapeutically-effective amount of a cytidine-containing compound.

2. The method of claim 1, wherein said stimulant is cocaine.

3. The method of claim 1, wherein said cytidine-containing compound is cytidine.

4. The method of claim 1, wherein said cytidine-containing compound further comprises choline.

5. The method of claim 1, wherein said cytidine-containing compound is CDP-choline.

6. The method of claim 1, wherein said cytidine-containing compound is CDP.

7. The method of claim 1, wherein said mammal is a human.

8. The method of claim 7, wherein said human is a pregnant woman or a child with antenatal exposure to a stimulant.

9. The method of claim 7, wherein said human has a stimulant craving.

10. The method of claim 7, wherein said human has a stimulant dependency.

11. A method of treating stimulant-induced cerebral vasoconstriction sequelae in a mammal, comprising administering to said mammal a therapeutically-effective amount of a cytidine-containing compound.

12. The method of claim 11, wherein said cerebral vasoconstriction results from exposure to cocaine.

13. The method of claim 11, wherein said cerebral vasoconstriction results from exposure to a substance that causes cerebral vasoconstriction.

14. The method of claim 11, wherein said mammal is a human.

15. The method of claim 11, wherein said cytidine-containing compound is cytidine.

16. The method of claim 11, wherein said cytidine-containing compound further comprises choline.

17. The method of claim 11, wherein said cytidine-containing compound is CDP-choline.

18. The method of claim 11, wherein said cytidine-containing compound is CDP.

19. A method of treating a mammal exposed to a stimulant, comprising administering to said mammal a therapeutically-effective amount of a cytosine-containing compound.

20. The method of claim 19, wherein said mammal is a human.

21. The method of claim 19, wherein said human is a pregnant woman or a child with antenatal exposure to a stimulant.

22. The method of claim 19, wherein said human has a stimulant craving.

23. The method of claim 19, wherein said human has a stimulant dependency.

24. A method of treating cerebral vasoconstriction sequelae in a mammal, comprising administering to said mammal a therapeutically-effective amount of a cytosine-containing compound.

25. The method of claim 24, wherein said cerebral vasoconstriction results from exposure to cocaine.

26. The method of claim 24, wherein said cerebral vasoconstriction results from exposure to a substance that causes cerebral vasoconstriction.

27. The method of claim 24, wherein said mammal is a human.

* * * * *